United States Patent
Wu (10) Patent No.: US 12,246,074 B2
(45) Date of Patent: Mar. 11, 2025

(54) GRANULOCYTE COLONY-STIMULATING FACTOR (GCSF) GENE THERAPY FOR TREATING NEUROLOGICAL DISEASES

(71) Applicant: CHS Pharma Inc., Naples, FL (US)

(72) Inventor: Jang-Yen Wu, Boca Raton, FL (US)

(73) Assignee: CHS Pharma Inc., San Francisco, CA (US)

( * ) Notice: Subject to any disclaimer, the term of this patent is extended or adjusted under 35 U.S.C. 154(b) by 1136 days.

(21) Appl. No.: 17/089,770

(22) Filed: Nov. 5, 2020

(65) Prior Publication Data

US 2021/0052745 A1 Feb. 25, 2021

Related U.S. Application Data

(63) Continuation of application No. PCT/US2019/033124, filed on May 20, 2019.

(60) Provisional application No. 62/674,049, filed on May 21, 2018.

(51) Int. Cl.

| A61K 38/00 | (2006.01) |
| A61K 48/00 | (2006.01) |
| A61P 25/28 | (2006.01) |
| C07K 14/535 | (2006.01) |
| C12N 15/86 | (2006.01) |

(52) U.S. Cl.
CPC .......... *A61K 48/0066* (2013.01); *A61P 25/28* (2018.01); *C07K 14/535* (2013.01); *C12N 15/86* (2013.01)

(58) Field of Classification Search
CPC ... A61K 48/0066; A61P 25/28; C07K 14/535; C12N 15/86
See application file for complete search history.

(56) References Cited

U.S. PATENT DOCUMENTS

| 2011/0091456 A1* | 4/2011 | McKenzie | A61K 39/3955 424/139.1 |
| 2012/0141420 A1* | 6/2012 | Schneider | A61K 38/193 424/93.2 |
| 2015/0322410 A1* | 11/2015 | Webster | C12N 15/86 435/320.1 |
| 2017/0128537 A1* | 5/2017 | Wagner | G01N 15/14 |

OTHER PUBLICATIONS

Minnerup et al. Stroke. 2008; 39:1855-1861. http://stroke.ahajournals.org; DOI: 10.1161/STROKEAHA.107.506816.*
Sanchez-Ramos et al. Neuroscience. Sep. 29, 2009; 163(1): 55-72. doi:10.1016/j.neuroscience.2009.05.071.*
Ren et al. Noninvasive tracking of gene transcript and neuroprotection after gene therapy. 2016, Gene Ther 23, 1-9.*
Ren, Jiaqian, et al.: "Noninvasive Tracking of Gene Transcript and Neuroprotection after Gene Therapy," Gene Ther., Jan. 2016, vol. 23 (1):1-9.
Shen, Fanxia, et al: "Adeno-Associated Viral Vector-Mediated Hypoxia-Inducible Vascular Endothelial Growth Factor Gene Expression Attenuates Ischemic Brain Injury After Focal Cerebral Ischemia in Mice," Stroke, Oct. 2006: 2601-2606.
Shevtsova, Z. et al.: "Promoters and serotypes: targeting of adeno-associated virus vectors for gene transfer in the rat central nervous system in vitro and in vivo," Exp Physiol, 2005, No. 90 (1):53-59.

* cited by examiner

*Primary Examiner* — Jeanette M Lieb
(74) *Attorney, Agent, or Firm* — Cuenot, Forsythe & Kim, LLC; Stanley A. Kim (57) ABSTRACT

Gene therapy using expression vectors containing a granulocyte colony-stimulating factor (GCSF) gene are able to protect cells in a cell-based as well as animal-based models for ischemic stroke.

9 Claims, 13 Drawing Sheets

*p < 0.05 vs 9 (AAV-CMV-GCSF), #p < 0.05 vs 5 (AAV-CMV-GFP)

*p < 0.05 vs 3 (AAV-CMV-GCSF)#p < 0.05 vs 6 (AAV-CMV- GCSF)

GRANULOCYTE COLONY-STIMULATING FACTOR (GCSF) GENE THERAPY FOR TREATING NEUROLOGICAL DISEASES

CROSS-REFERENCE TO RELATED APPLICATIONS

The present application is a by-pass continuation under 35 U.S.C. 111(a) of international patent application number PCT/US2019/033124 filed on May 20, 2019 which claims the priority of U.S. provisional patent application Ser. No. 62/674,049, filed on May 21, 2018.

STATEMENT AS TO FEDERALLY SPONSORED RESEARCH

Not applicable.

FIELD OF THE INVENTION

The invention relates to the fields of molecular biology, gene therapy, and neurology.

BACKGROUND

Neurological diseases such as stroke and AD are significant causes of morbidity and mortality throughout the world. Administration of tissue plasminogen activator (tPA) is the standard of care treatment for acute ischemic stroke patients. By clearing the obstructing clot, tPA restores blood flow and thereby prevents further damage to brain tissue caused by lack of oxygen. Unfortunately, tPA remains the only FDA-approved drug for treating acute ischemic stroke. Medications for treating the symptoms of AD include cholinesterase inhibitors, and an N-methyl D-aspartate antagonist (memantine). These, however, are of limited efficacy. While extensive efforts have been made to develop new therapies for treating stroke and AD, little progress has been achieved.

SUMMARY

It has been discovered that gene therapy using expression vectors containing a granulocyte colony-stimulating factor (GCSF) gene are able to prevent and treat the pathological sequalae of stroke and AD.

Accordingly, described herein are the use of, compositions for, and methods of using, GCSF gene therapy for preventing or treating the sequelae of a neurological disease such as ischemic stroke or AD in a subject. The GCSF gene therapy can include the use of a viral vector that encodes a GCSF gene. The viral vector can include a neuron-specific promoter operatively linked with the GCSF gene such that the GCSF gene is expressed preferentially or exclusively in neurons after the gene therapy is administered. The viral vector can include an hypoxia-sensitive gene switch/biosensor operatively linked with the GCSF gene which causes the GCSF gene to be preferentially or exclusively in hypoxic cells after the gene therapy is administered.

In the uses, compositions, and methods described herein the neurological disease can be ischemic stroke, and the gene therapy can be started before or after (e.g., within at least 30 min, 45 min, 1 h, 2 h, 3 h, 4 h, 5 h, or 6 h) the ischemic stroke. The gene therapy reduces brain neuron death in the subject caused by hypoxia, reduce the amount of neurological deficit in the subject caused by the stroke, and/or reduce the volume of a brain infarct that develops in the subject after the stroke compared to the volume of the brain infarct that would develop in the subject if the subject did not receive the gene therapy. The gene therapy for stroke can stimulate neurogenesis in the brain of the subject, and can involve the use of a recombinant adeno-associated virus including a gene encoding human GCSF protein.

In the uses, compositions, and methods described herein the neurological disease can be AD. The gene therapy for AD can reduce amyloid-β (Aβ) levels in brain neurons in the subject, and/or reduce the amount of neurological deficit in the subject caused by the AD. The gene therapy can reduce Beclin 1 levels in brain neurons in the subject, protect mitochondrial function in brain neurons in the subject, increase expression of choline acetyltransferase (ChAT) in brain neurons in the subject, and/or stimulates neurogenesis in the brain of the subject. The gene therapy for AD can stimulate neurogenesis in the brain of the subject, and can involve the use of a recombinant adeno-associated virus including a gene encoding human GCSF protein.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, 27th Edition, Lippincott, Williams & Wilkins, 2000.

Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DETAILED DESCRIPTION

Disclosed herein are methods and compositions for expressing GCSF in a target tissue or cell to treat or prevent one or more of the sequelae that occur in stroke and AD. While GCSF protein might be administered directly to a target tissue, for more controlled delivery of the agent, gene therapy methods are preferred. Gene therapy agents that express GCSF in an inducible (e.g., in response to hypoxia) and tissue-specific (in neurons or other brain cells) are preferred. Gene therapy agents typically are vectors that contain a gene encoding GCSF (e.g., a human GCSF gene) can be used to introduce and express GCSF in a target cell. Several are known in the art including viral vectors and non-viral vectors. More than one promoter can be present in a vector, and hence more than one gene can be expressed by a vector. Further, the vector can include a sequence which encodes a signal peptide or other moiety which facilitates the secretion of the heterologous gene product from the host cell.

Viral vectors that exhibit low toxicity to the host cell and are capable of producing high levels of a transgene (e.g., a GCSF gene) are preferred as such vectors have been extensively studied and characterized. Examples of viral vector methods and protocols are reviewed in Kay et al. Nature Medicine 7:33-40, 2001.

Adeno-associated virus (AAV) vectors are presently preferred viral vectors for use in the methods described herein because they have proven to be safe, stable and capable of providing long-lasting transgene expression in other applications. Moreover, AAV vectors are able to efficiently transduce a number of different target cells and can integrate into a host cell's genome in a site-specific manner. Methods for use of AAV vectors are discussed, for example, in Tal, J., J. Biomed. Sci. 7:279-291, 2000 and Monahan and Samulski, Gene Therapy 7:24-30, 2000.

AAV vectors for use in the methods and compositions described herein are nucleic acid sequences that include those AAV sequences required in cis for replication and packaging (e.g., functional TRs) of the DNA into a virion. Useful AAV vectors have one or more of the AAV WT genes deleted in whole or in part, but retain functional flanking TR sequences. The AAV nucleic acids, proteins, vectors, and virions used in the invention may be derived from any of several AAV serotypes including 1, 2, 3, 4, 5, 6, 7, and 8. Genes from these serotypes can be isolated using standard methods (Chiorini et al., J Virol. 73:1309-19, 1999; Rutledge et al., J Virol. 72:309-19, 1998; Xiao et al., J Virol. 73:3994-4003, 1999; Muramatsu et al., Virology 221:208, 1996; and Chiorini, et al., J. Virol. 71:6823, 1997; Sambrook and Russell supra). Vectors containing rep genes and TRs derived from serotype 2 are particularly preferred because serotype 2 vectors have been characterized in great detail and constructs derived from serotype 2 are commonly available. Particular AAV vectors and AAV proteins of different serotypes are discussed in Chao et al., Mol. Ther. 2:619-623, 2000; Davidson et al., Proc. Nat'l Acad. Sci. USA 97:3428-3432, 2000; and Xiao et al., J. Virol. 72:2224-2232, 1998.

Also useful in the system of the invention are AAV virions that have mutations within the virion capsid. For example, suitable AAV mutants may have ligand insertion mutations for the facilitation of targeting AAV virions to specific cell types (e.g., neurons or other brain cells). Pseudotyped AAV virions that have mutations within the capsid may also be used in compositions and methods of the invention. Pseudotyped AAV virions contain an rAAV vector derived from a particular serotype that is encapsidated within a capsid containing proteins of another serotype. Methods of making AAV capsid mutants are known, and include site-directed mutagenesis (Wu et al., J. Virol. 72:5919-5926); molecular breeding, nucleic acid, exon, and DNA family shuffling (Soong et al., Nat. Genet. 25:436-439, 2000; Coco et al., Nature Biotech. 2001; 19:354; and U.S. Pat. Nos. 5,837,458; 5,811,238; and 6,180,406; Kolkman and Stemmer, Nat. Biotech. 19:423-428, 2001; Fisch et al., Proc. Nat'l Acad. Sci. USA 93:7761-7766, 1996; Christians et al., Nat. Biotech. 17:259-264, 1999); ligand insertions (Girod et al. Nat. Med. 9:1052-1056, 1999); cassette mutagenesis (Rueda et al. Virology 263:89-99, 1999; Boyer et al., J. Virol. 66:1031-1039, 1992); and the insertion of short random oligonucleotide sequences.

In addition to AAV, adenoviral (Ad) vectors, Herpes Simplex Virus (HSV), retroviral vectors, lentiviral vectors, Alphaviruses, and other known viral vectors might also be used in the methods and compositions described herein. Variants of such vectors such as vectors containing tissue-specific (e.g., neuron) enhancers and promoters operably linked to nucleotide sequences encoding GCSF are also within the invention. Methods for using recombinant Ad as gene therapy vectors are discussed, for example, in W. C. Russell, Journal of General Virology 81:2573-2604, 2000, and Bramson et al., Curr. Opin. Biotechnol. 6:590-595, 1995. Methods for use of HSV vectors are discussed, for example, in Cotter and Robertson, Curr. Opin. Mol. Ther. 1:633-644, 1999. Methods for use of retrovirus-based vectors are discussed, for example, in Hu and Pathak, Pharmacol. Rev. 52:493-511, 2000 and Fong et al., Crit. Rev. Ther. Drug Carrier Sy st. 17:1-60, 2000. Methods for use of lentiviral vectors are discussed, for example, in Vigna and Naldini, J. Gene Med. 5:308-316, 2000 and Miyoshi et al., J. Virol. 72:8150-8157, 1998. Methods for use of Alphaviruses are described, for example, in Lundstrom, K., Intervirology 43:247-257, 2000 and Perri et al., Journal of Virology 74:9802-9807, 2000.

Several non-viral methods for introducing nucleic acids (e.g., those encoding GCSF) into host cells might also be used in the invention. For a review of non-viral methods, see Nishikawa and Huang, Human Gene Ther. 12:861-870, 2001 and M. I. Phillips, Gene Therapy Methods, Academic press, 2002. Methods involving physical techniques for the introduction of a vector system into a host cell can be adapted for use in the present invention. The particle bombardment method of gene transfer involves an Accell device (i.e., gene gun) to accelerate DNA-coated microscopic gold particles into target tissue, including the brain. Particle bombardment methods are described in Yang et al., Mol. Med. Today 2:476-481 1996 and Davidson et al., Rev. Wound Repair Regen. 6:452-459, 2000. Cell electropermeabilization (also termed cell electroporation) may be employed. This technique is discussed in Preat, V., Ann. Pharm. Fr. 59:239-244 2001 and involves the application of pulsed electric fields to cells to enhance cell permeability, resulting in exogenous polynucleotide transit across the cytoplasmic membrane.

Synthetic gene transfer molecules can be designed to form multimolecular aggregates with plasmid DNA and to bind the resulting particles to the target cell (e.g., a neuron) surface in such a way as to trigger endocytosis and endosomal membrane disruption. Polymeric DNA-binding cations (including polylysine, protamine, and cationized albumin) can be linked to neuron-specific targeting ligands and trigger receptor-mediated endocytosis into neurons. Methods involving polymeric DNA-binding cations are reviewed in Guy et al., Mol. Biotechnol. 3:237-248, 1995 and Garnett, M. C., Crit. Rev. Ther. Drug Carrier Syst. 16:147-207, 1999. Cationic amphiphiles, including lipopolyamines and cationic lipids, may provide receptor-independent transfer of the therapeutic gene (e.g., a GCSF gene) into target cells (e.g., neurons). Preformed cationic liposomes or cationic lipids may be mixed with plasmid DNA to generate cell-transfecting complexes. Methods involving cationic lipid formulations are reviewed in Felgner et al., Ann. N.Y. Acad. Sci. 772:126-139, 1995 and Lasic and Templeton, Adv. Drug Delivery Rev. 20:221-266, 1996. Suitable methods can also include use of cationic liposomes as agents for introducing DNA or protein into cells. For therapeutic gene delivery, DNA may also be coupled to an amphipathic cationic peptide (Fominaya et al., J. Gene Med. 2:455-464, 2000).

Methods that involve both viral and non-viral based components may be used in the methods and compositions described herein. An Epstein Barr Virus (EBV)-based plasmid for therapeutic gene delivery is described in Cui et al., Gene Therapy 8:1508-1513, 2001. A method involving a DNA/ligand/polycationic adjunct coupled to an Ad is described in Curiel, D. T., Nat. Immun. 13:141-164, 1994.

Other techniques according to the invention may be based on the use of tissue (e.g., brain)-specific ligands. Synthetic peptides or polypeptides may be used as ligands in targeted delivery of DNA and proteins to brain cell-specific receptors. Complexes of protein and ligand or plasmid DNA and ligand can mediate protein and DNA transfer into brain cells. Gene-bearing microbubbles, when exposed to ultrasound, cavitate and locally release a therapeutic agent. Attachment of a brain cell-targeting moiety to the contrast agent vehicle may result in site-specific (e.g., brain) therapeutic gene expression.

The vector system described herein can include a gene switch/biosensor to sense the presence of a stimulus (e.g., low oxygen) and relay a message to another component of the system to start or increase expression of a heterologous gene. In the hypoxia-sensing, neuro-protective AAV vector system described herein, the gene switch/biosensor can include a hypoxia-inducible factor (HIF) such as HIH-1 and a hypoxia-response element (HRE) in the promoter of the GCSF gene. A number of other gene switch/biosensors might be used in the vectors described herein. For example, switch responsive to high or low levels of glucose or those responsive to one or more inflammatory cytokines can be constructed, e.g., by replacing the ODD portion of the HIF with another element that is sensitive to another stimulus.

In the methods and compositions described herein, tissue-specific regulatory elements might be used to direct tissue-specific expression of other elements of the system, e.g., the gene switch/sensor or the GCSF gene might. To illustrate, to express genes specifically in the neuronal tissue, one or more neuron-specific regulatory elements can be used. An example of a neuron-specific promoter is the synapsin promoter. Examples of other neuron-specific promoters include the Hb9, CamkII, and MeCP2 promoters. Brain-specific promoters that might be used include the thy-1 antigen and gamma-enolase promoters as wells as the glial-specific glial fibrillary acidic protein (GFAP) gene promoter, and the human FGF1 gene promoter (Chiu et al., Oncogene 19:6229-6239, 2000).

Examples of other regulatory sequences that may be used in vectors of the invention include insulators, silencers, enhancers (e.g., one or more neuron-specific enhancers), initiation sites, termination signals, internal ribosome entry sites (IRES s) and polyA tails.

The compositions and methods described herein are useful for preventing or reducing one or more sequelae of stroke (e.g., edema, hemorrhagic transformation, intracranial pressure, breakdown of the blood-brain-barrier, infarct volume, and the resulting neurological deficit in the subject) or AD (e.g., Aβ accumulation, tau tangle formation, inflammation, nerve cell death, and the resulting neurological deficit in the subject). Successful treatment of stroke and AD can be evaluated according to established methods. These include neurological examination, computed tomography, magnetic resonance imaging, and cerebral angiography. The mammalian subject might be any that has suffered, is suffering from, or is at risk of developing cerebral ischemia (e.g., ischemic stroke, transient ischemic attack, or subarachnoid hemorrhage) or AD (e.g., age, family history, genetics, head injury, heart disease, diabetes, stroke, high blood pressure and high cholesterol) including, human beings. Human subjects might be male, female, adults, children, seniors (65 and older), and those with other diseases or risk factors for cerebral ischemia or AD.

The compositions described herein may be administered to animals including human beings in any suitable formulation by any suitable method. For example, recombinant AAV virions (i.e., particles) may be directly introduced into an animal, including by intravenous injection, administration to the cerebrospinal fluid, or in situ injection into target tissue (e.g., brain tissue). For example, a conventional syringe and needle can be used to inject an rAAV virion suspension into an animal. Depending on the desired route of administration, injection can be in situ (i.e., to a particular tissue or location on a tissue), intrathecal, intravenous, or by another parenteral route. Parenteral administration of virions by injection can be performed, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the rAAV virions may be in powder form (e.g., lyophilized) for constitution with a suitable vehicle, for example, sterile pyrogen-free water, before use.

To facilitate delivery of the rAAV virions to an animal, the virions of the invention can be mixed with a carrier or excipient. Carriers and excipients that might be used include saline (especially sterilized, pyrogen-free saline) saline buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly preferred for delivery of virions to human subjects. Methods for making such formulations are well known and can be found in, for example, Remington's Pharmaceutical Sciences.

In addition to the formulations described previously, the virions can also be formulated as a depot preparation. Such long acting formulations may be administered by implantation. Thus, for example, the virions may be formulated with suitable polymeric or hydrophobic materials (for example as an emulsion in an acceptable oil) or ion exchange resins, or as sparingly soluble derivatives.

Effective Doses

The compositions described herein are preferably administered to a mammal in an effective amount, that is, an amount capable of producing a desirable result in a treated subject (e.g., protecting neurons from damage or generating new neurons in the subject). Such a therapeutically effective amount can be determined as described below.

Toxicity and therapeutic efficacy of the compositions described herein can be determined by standard pharmaceutical procedures, using either cells in culture or experimental animals to determine the LD50 (the dose lethal to 50% of the population) and the ED50 (the dose that produces the desired effect). The dose ratio between toxic and therapeutic effects is the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of preferred compositions lies preferably within a range that includes an ED50 with little or no toxicity. The dosage may vary within this range depending upon the dosage form employed and the route of administration utilized.

As is well known in the medical and veterinary arts, dosage for any one animal depends on many factors, including the subject's size, body surface area, age, the particular composition to be administered, time and route of administration, general health, and other drugs being administered concurrently. It is expected that an appropriate dosage for intravenous or in situ administration of the compositions would be in the range of about 5 µl/kg at $10^{13}$ particles and 50 µl/kg at $10^{12}$ particles. For a 70 kg human a 3 ml injection of $10^{12}$ particles is presently believed to be an appropriate dose.

EXAMPLES

Figure 1:
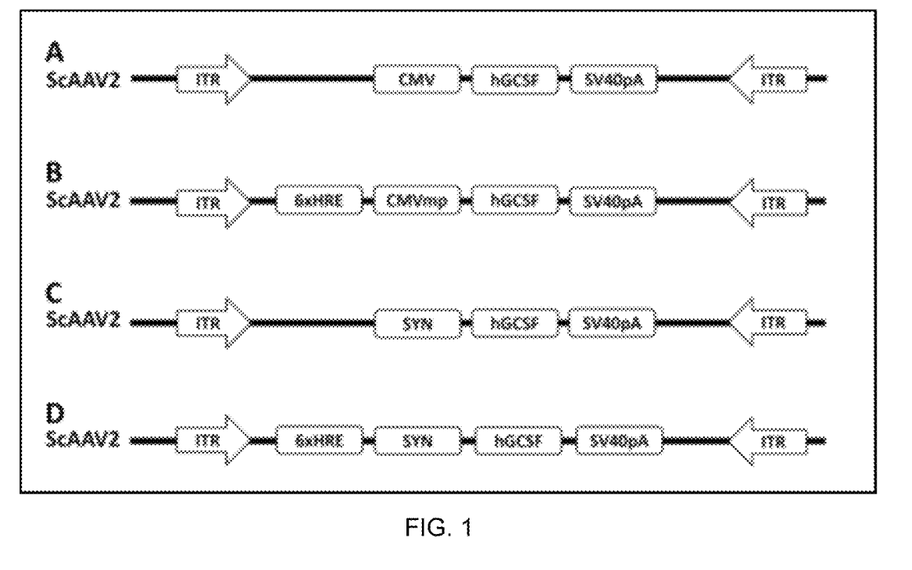
FIG. 1 is a schematic diagram of vectors used in the research described herein.

In the schematic diagram of vectors shown in FIG. 1, the promoter elements and human GCSF cDNA were incorporated into self-complementary AAV2 (scAAV2). In FIG. 1, (A) depicts a vector containing the CMV promoter together with the human GCSF cDNA coding sequence (AAV-CMV-GCSF); (B) depicts a vector containing the hypoxia regulated sequence (HRE) together with the minimal CMV promoter (CMVmp) in addition to the GCSF cDNA coding sequence (AAV-HRE-CMV-GCSF); (C) depicts a vector containing the synapsin promoter together with the GCSF cDNA coding sequence (AAV-SYN-GCSF); and (D) depicts a vector containing the hypoxia regulated sequence together with the synapsin promoter in addition to the GCSF coding sequence (AAV-HRE-SYN-GCSF). A SV40 poly A (SV40pA) sequence and inverted terminal repeat sequences (ITR) were present in scAAV vectors. AAV-CMV-GCSF drives constitutive expression of GCSF. AAV-HRE-CMV-GCSF restricts expression of GCSF to hypoxic (e.g., ischemic) tissue. AAV-SYN-GCSF restricts the expression of GCSF to neuronal tissue. AAV-HRE-SYN-GCSF restricts the expression of GCSF to hypoxic neuronal tissue.

Figure 2:
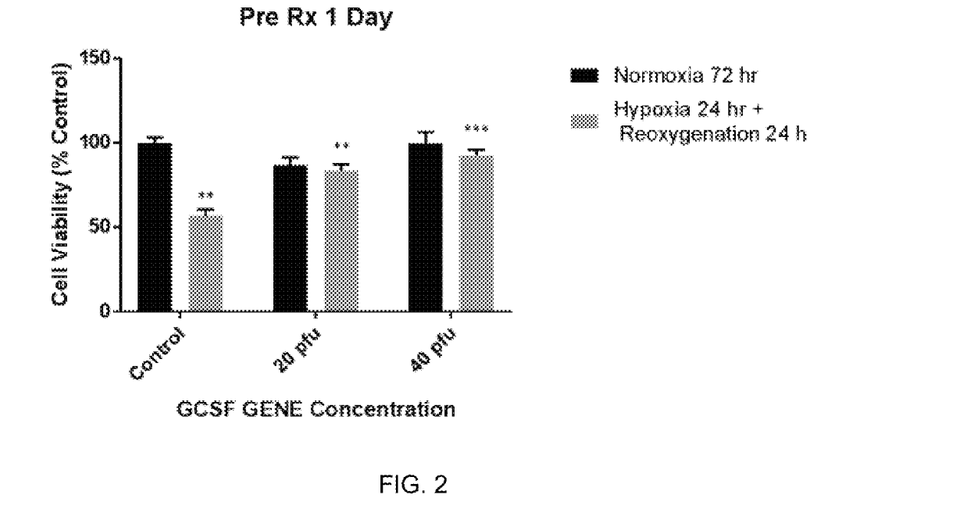
FIG. 2 is a graph showing protection of PC12 cells against cell death from hypoxia/re-oxygenation using AAV-GCSF gene therapy.

The protection of PC12 cells against cell death from hypoxia/re-oxygenation using AAV-GCSF gene therapy is shown in FIG. 2. Percentage cell viability was determined in PC12 cells under normoxic conditions or in cells subjected to 24 hours of hypoxia with 24 hours of re-oxygenation. Cell viability was decreased to about 55% in control untreated cells (p<0.01, n=6), whereas in cultures treated with either 20 pfu/cell or 40 pfu/cell of AAV-CMV-GCSF gene there was no significant decrease in viability following hypoxia/re-oxygenation exposure.

Figure 3:
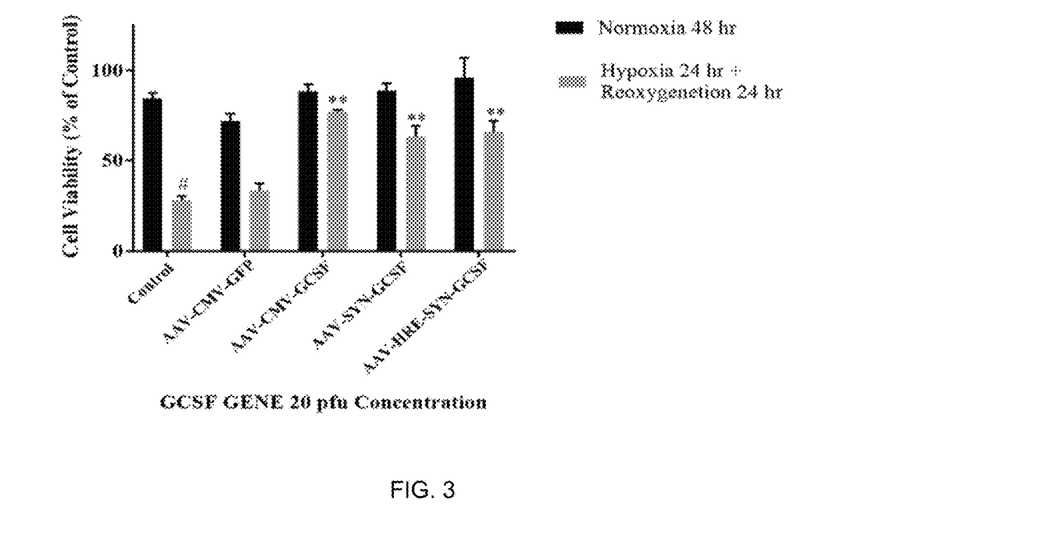
FIG. 3 is a graph showing the results of an ATP viability assay for AAV-CMV-GCSF plasmid transfected undifferentiated PC12 cells subjected to 24 hours of hypoxia.

The results of an ATP viability assay for AAV-CMV-GCSF plasmid-transfected undifferentiated PC12 cells subjected to 24 hours of hypoxia is shown in FIG. 3. Undifferentiated PC12 cells were transfected with AAV-CMV-GCSF plasmid and subsequently treated with 24 hours of hypoxia (N=5 at each time point). PC-12 cells were pretreated with GCSF gene for 24 hours to express in cells and then exposed to 24-hour hypoxia followed by 24-hour re-oxygenation. Cell viability was measured using an ATP assay. Control values were fixed at 100%. The values for Hypoxia and GENE+Hypoxia were normalized relative to the control values and represent mean±SEM of 5 preparations. (All data are presented as mean+/−SEM, #P<0.05, significantly different compared with control treated cells. *P<0.05, significantly different compared with AAV-CMV-GFP-treated cells. One-way ANOVA, Post hoc Tukey). AAV-CMV-GCSF, AAV-SYN-GCSF and AAV-HRE-SYN-GCSF all showed significant protection against hypoxia-re-oxygenation-induced cell death compared to the control or the AAV-CMV-GFP (vector contains the gene for Green Fluorescent Protein rather than GCSF) group.

Figure 4A:
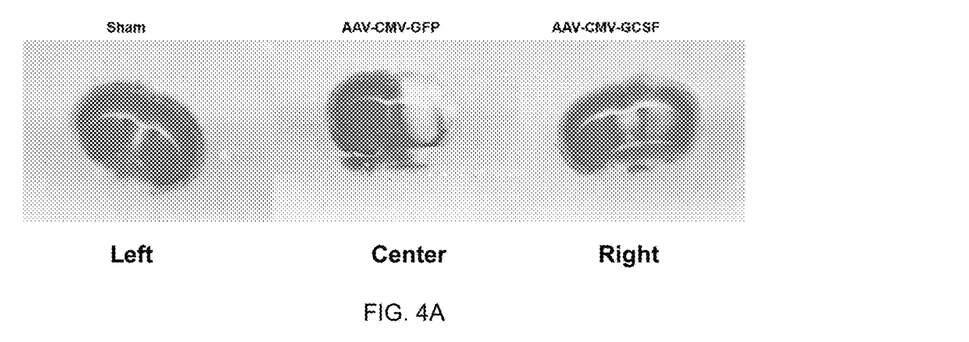
FIG. 4A is a series of photomicrographs showing the effect of GCSF gene therapy on ischemic infarct in bilateral carotid artery occlusion (BCAO) mouse stroke model.

The effect of GCSF gene therapy on ischemic infarct in Bilateral Carotid Artery Occlusion (BCAO) mouse stroke model is shown in FIG. 4A. Infarct volumes were visualized by using 2% TTC staining. In the BCAO method, mice were anesthetized and then kept at a constant temperature of 36+/−1° C. A ventral cervical midline incision was carried out to expose the carotid arteries which were then occluded with microaneurism clips. Cerebral ischemia was induced by 30 or 0 minutes of BCAO. At the end of the period of ischemia, the microaneurism clips were removed and the incision was sutured closed. With the exception of applying the microaneurism clips, the same procedure was performed in sham operated animals. In FIG. 4A, mice were either sham operated (Left), or BCAO operated and treated with AAV-CMV-GFP (vehicle) (Center), or BCAO-operated and treated with AAV-CVM-GCSF (Right). Vectors were administered in left eye (1.5 µl containing 3×10E9 plaque-forming unit) 30 mins-60 mins after BCAO. Animals were sacrificed 7 days after BCAO. AAV-CMV-GCSF-treated animals showed a marked reduction in the infarction size (Right) compared to the control (Center), indicating that GCSF gene therapy was effective in protecting brain from BCAO-induced injury.

Figure 4B:
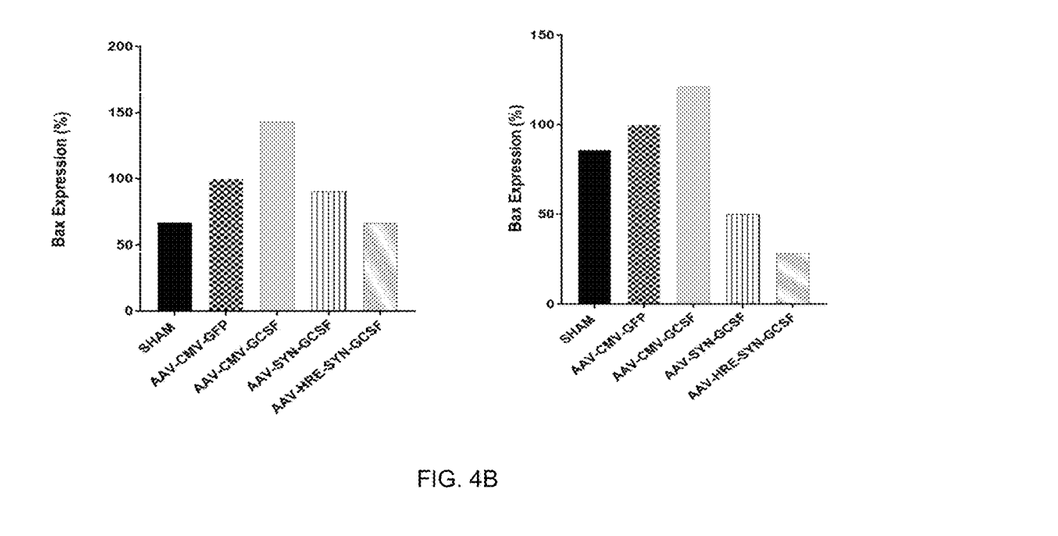
FIG. 4B is a series of graphs showing the effect of G-CSF gene therapy on the expression of Bax.
Figure 5:
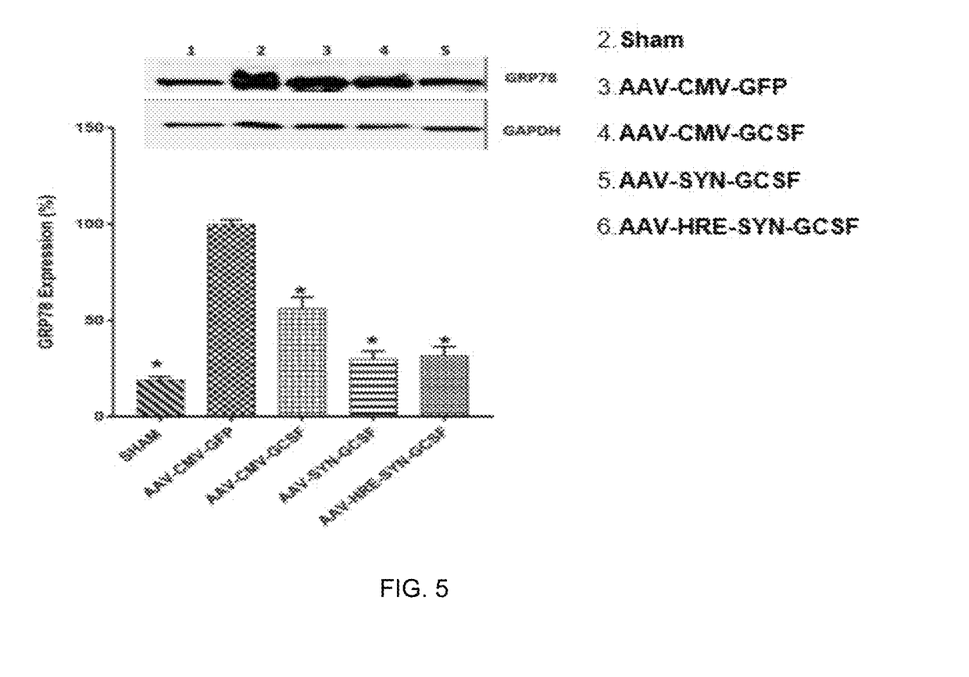
FIG. 5 is a Western blot and a graph showing the effect of G-CSF gene therapy on the expression of GRP78 four days after BCAO.
Figure 6:
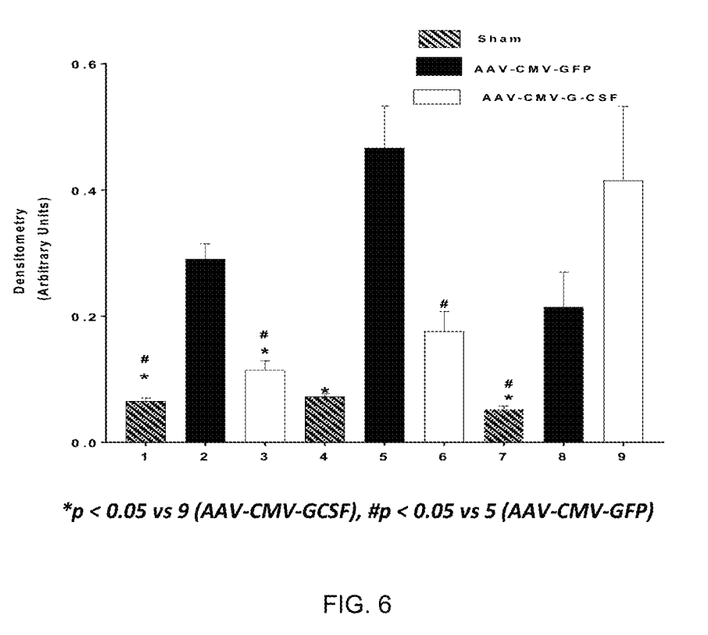
FIG. 6 is a graph showing the effect of AAV-CMV-G-CSF on pIRE1 and IRE1 expression in BCAO mice.
Figure 7:
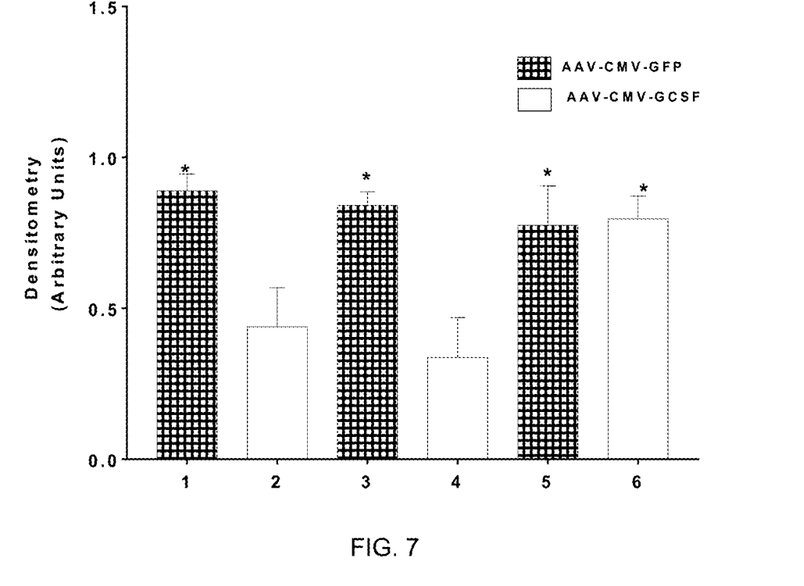
FIG. 7 is a graph showing the effect of AAV-CMV-G-CSF on XBP-1 expression in BCAO mice.
Figure 8:
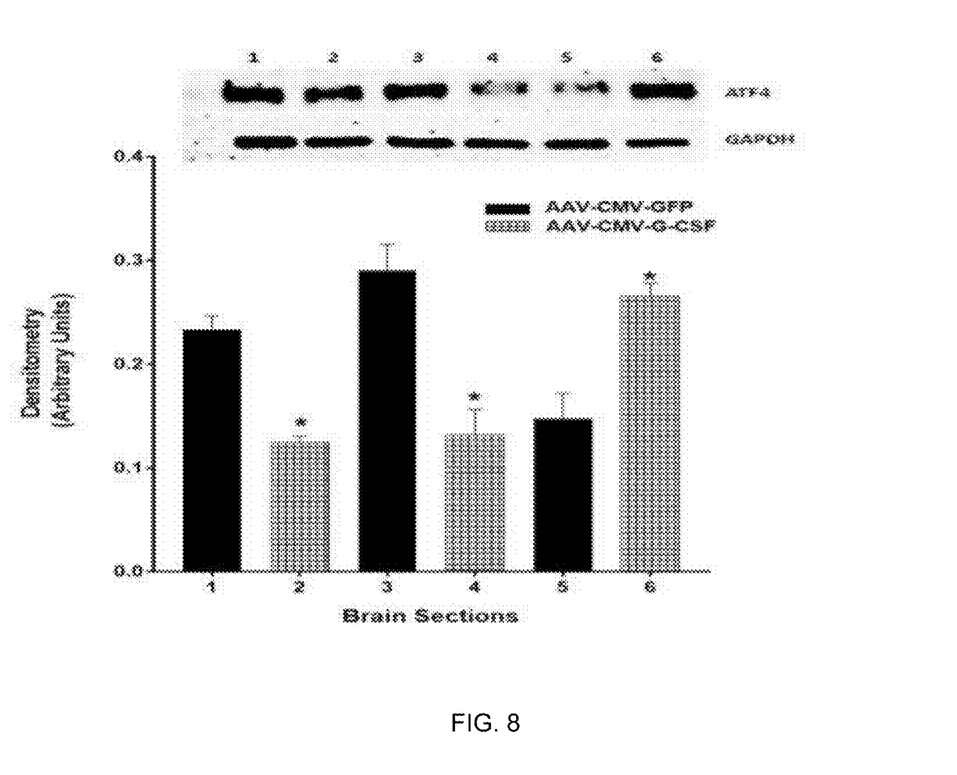
FIG. 8 is a Western blot and a graph showing the effect of AAV-CMV-G-CSF on ATF4 expression in BCAO mice.
Figure 9:
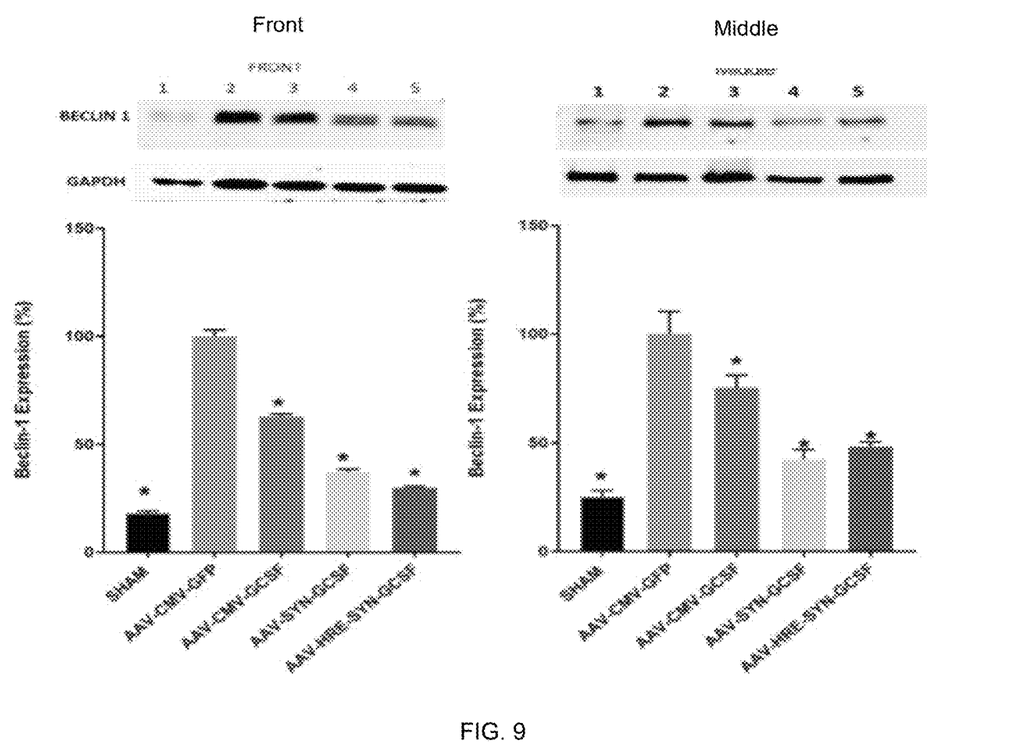
FIG. 9 is Western blots and graphs showing the effect of GCSF gene therapy on the expression of Beclin-1 seven days after BCAO.
Figure 10:
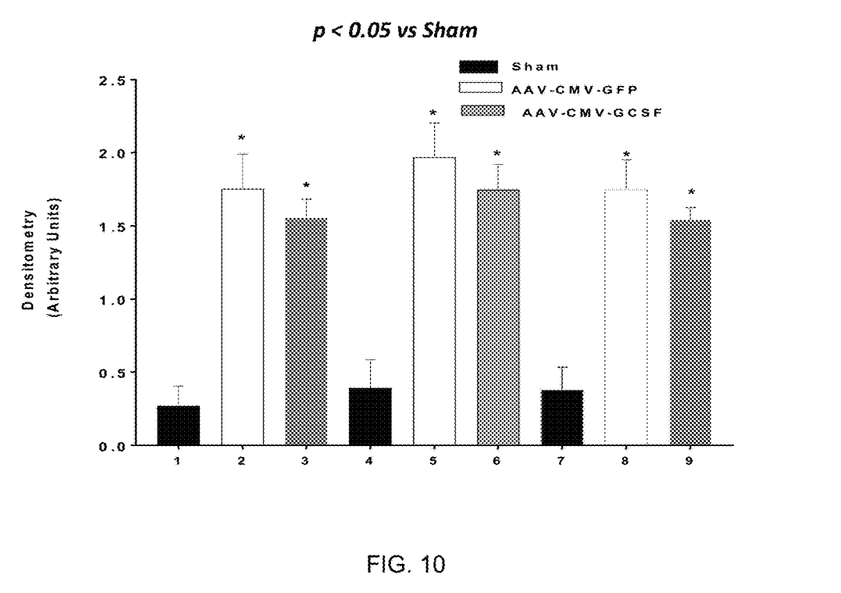
FIG. 10 is a graph showing the effect of AAV-CMV-G-CSF on DRP1 expression in BCAO mice.
Figure 11:
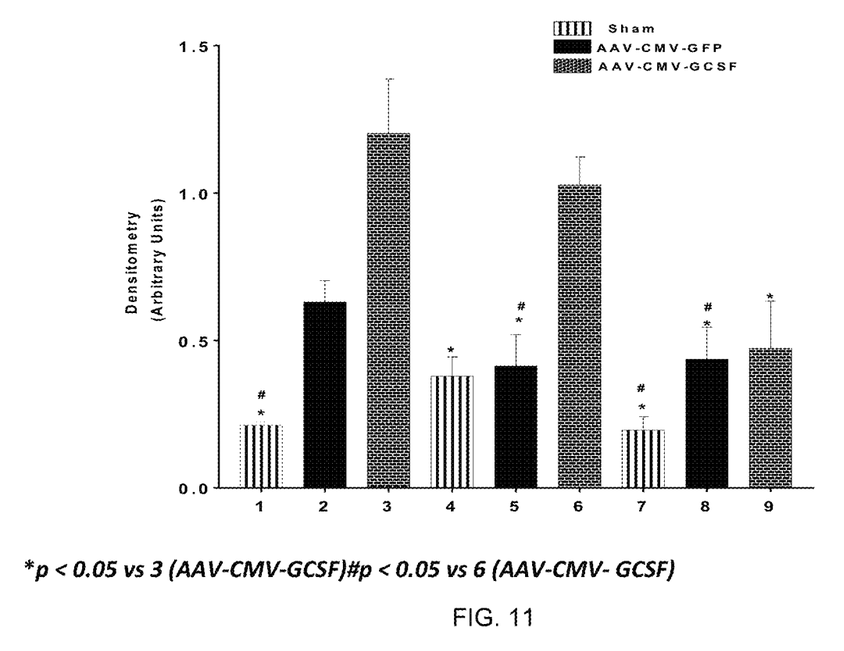
FIG. 11 is a graph showing the effect of AAV-CMV-G-CSF on OPA1 expression in BCAO mice.

The effect of GCSF gene therapy on the expression of Bax, a pro-apoptosis biomarker, as measured by Western blotting is shown in FIG. 4B. A decrease in Bax expression of approximately 10% and 40% in the front and 50% and 75% in the hind brain region by AAV-SYN-GCSF and AAV-HRE-SYN-GCSF gene therapy, respectively, was observed. Similar experiments were performed for other biomarkers. As shown in FIG. 5, a decrease in the endoplasmic reticulum (ER) stress biomarker, GRP78, of approximately 30% 35% and 50% by AAV-CMV-GCSF, AAV-SYN-GCSF and AAV-HRE-SYN-GCSF gene therapy, respectively, was observed. As shown in FIG. 6, pIRE1, the active form of an ER stress biomarker, was greatly reduced in both front and mid-brain region by AAV-CMV-GCSF treatment compared to the treatment with control vector, AAV-CMV-GFP. As shown in FIG. 7, XBP1 was reduced substantially in both the front and mid-brain region in AAV-CMV-GCSF treated group compared to the group treated with the control vector, AAV-CMV-GFP. As shown in FIG. 8, ATF4, the downstream PERK pathway component of ER stress, was reduced by approximately 35% and 50% in front and middle brain, respectively, in BCAO mice infected with AAV-G-CSF by comparison to AAV-GFP treated control group. As shown in FIG. 9, the autophagy stress marker, Beclin1, showed a reducing trend for the AAV-CMV-GCSF—treatment (lane 2), in the frontal section (4 cm from the frontal pole) of the brain compared to AAV-CMV-GFP (vehicle; lanes 2). Referring to FIG. 10, neuro-protection of GCSF gene therapy in the BCAO model was demonstrated by a decrease of DRP1, a marker of mitochondrial stress. AAV-CMV-GCSF gene treatment reduced the DRP1 level by about 20% compared to the AAV-CMV-GFP control group. As shown in FIG. 11, contrary to the mitochondrial stress biomarker, DRP1, the marker of mitochondrial enhancer, OPA1 was greatly elevated by about 45, 60 and 5%, respectively in the front, mid and hind brain compared to the AAV-CMV-GFP treated group.

Figure 12:
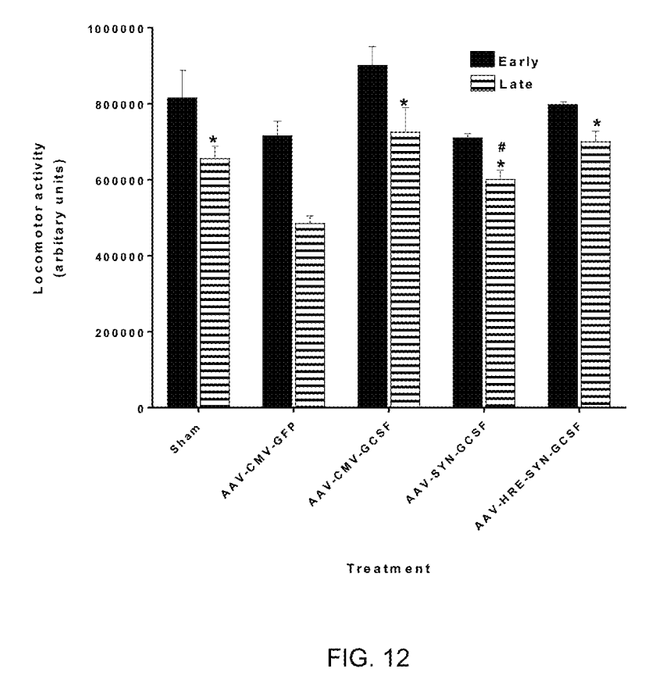
FIG. 12 is a graph showing neuroprotection by AAV-CMV-GCSF in BCAO mice was measured by locomotor activity test.
Figure 13:
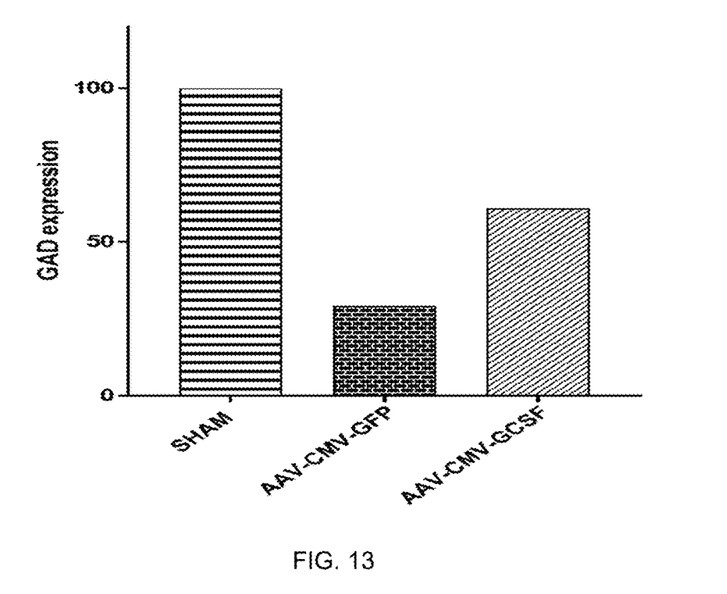
FIG. 13 is a graph showing the effect of GCSF gene therapy on GABA neurons identified by immunohistochemical localization in BCAO mouse stroke model.
Figure 14:
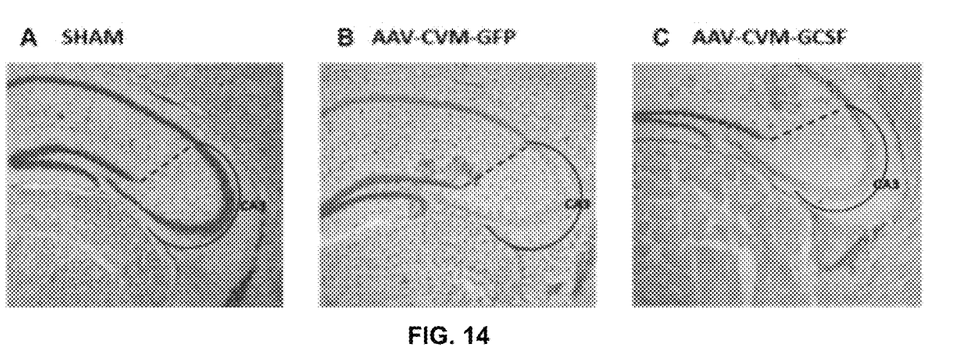
FIG. 14 is a series of photomicrographs showing NissI body staining in animals treated with GCSF gene therapy and controls.
Figure 15:
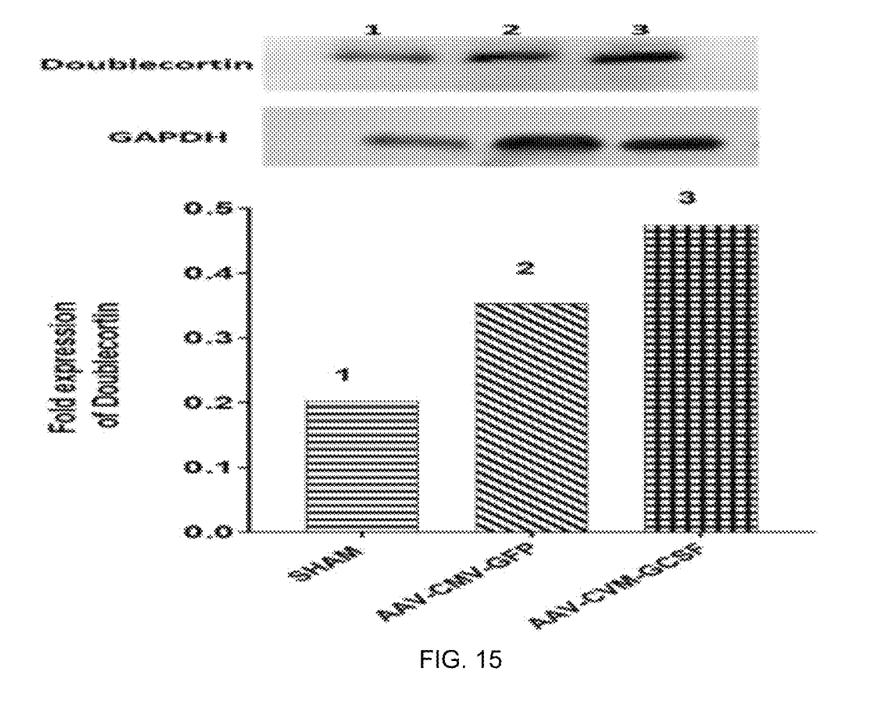
FIG. 15 is a Western blot and a graph showing the effect of AAV-CMV-G-CSF on doublecortin expression at four days after BCAO.
Figure 16:
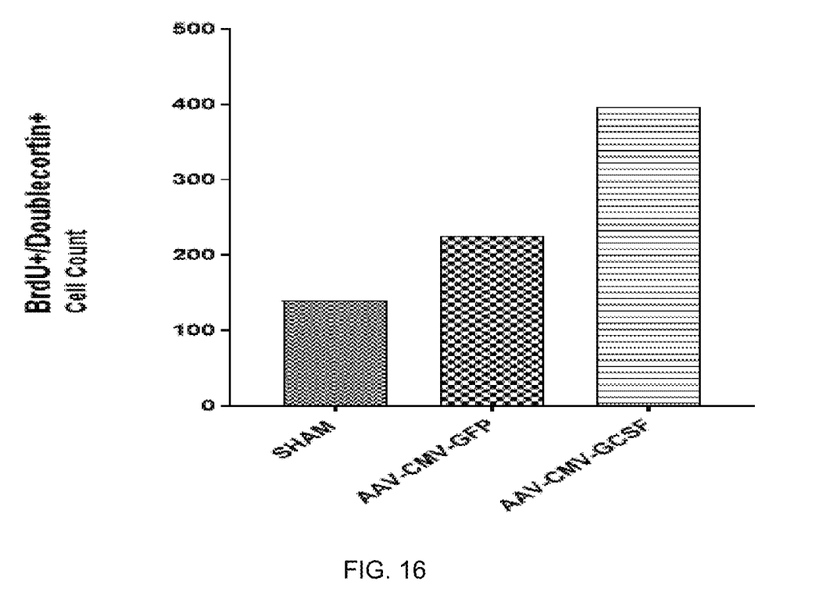
FIG. 16 is a graph showing the production of new immature neurons in the Dentate Gyms in BCAO mice treated with GCSF gene therapy.

Referring to FIG. 12, neuro-protection of GCSF gene therapy in the BCAO model was demonstrated in the locomotor activity test. AAV-SYN-GCSF and AAV-HRE-SYN-GCSF gene therapy improved the locomotor activity significantly compared to the group treated with the control vector, AAV-CMV-GFP, in BCAO stroke model. Referring to FIG. 13, neuro-protection of GCSF gene therapy in the BCAO model was demonstrated by an increase in GABA neurons after treatment with AAV-CMV-GCSF gene therapy. GABA neurons, identified as glutamate decarboxylase (GAD) positive neurons, increased by 50% in the AAV-CMV-GCSF gene therapy treated group compared to the group treated with the control vector, AAV-CMV-GFP. As shown in FIG. 14, an increase of neurons in hippocampus was shown by Nissl staining. Neurogenesis in BCAO stroke model after AAV-GCSF gene therapy by immunofluorescence staining using specific antibodies to Nestin (green fluorescence), a marker for neural stem cells/neural progenitors and Ki67 (red fluorescence), a biomarker of cell proliferation; an increase in doublecortin (FIG. 15) a biomarker for immature neurons in the AAV-CMV-GCSF mice. The production of new immature neurons in the Dentate Gyrus in BCAO mice treated with GCSF gene therapy was also shown using double immunofluorescence of Bromodeoxyuridine (BrdU) and Doublecortin (DCX) (FIG. 16) and triple immunofluorescence of BrdU, DCX and NeuN. The production of new immature neurons (BrdU+/DCX+ cells).

Figure 17:
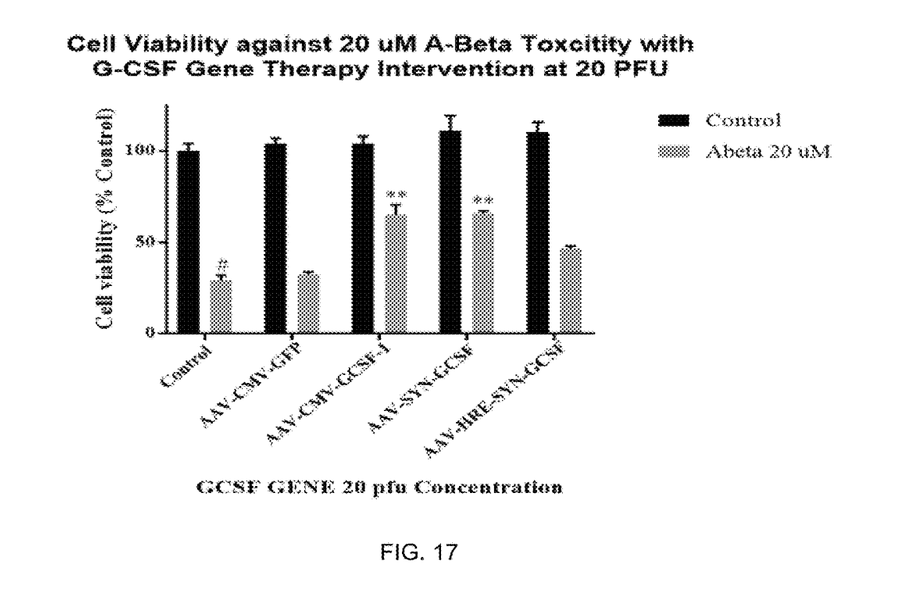
FIG. 17 is a graph showing the effect of GCSF gene therapy on β-amyloid (Aβ 25-35)—induced cell toxicity in cell-based model for AD.

Referring to FIG. 17, neuro-protection of GCSF gene therapy as assessed by Aβ-induced toxicity in PC-12 cells, a cell-based model for AD, was observed. At 20 pfu concentration, AAV-CMV-GCSF, AAV-SYN-GCSF and AAV-HRE-SYN-GCSF increased cell viability from 30% to 65%, 65% and 50%, respectively, compared with the group treated with the control vector, AAV-CMV-GFP. GCSF protein also attenuated Aβ-induced toxicity in PC-12 cells in a dose-dependent manner reaching a maximum protection at 25 ng/ml.

Figure 18:
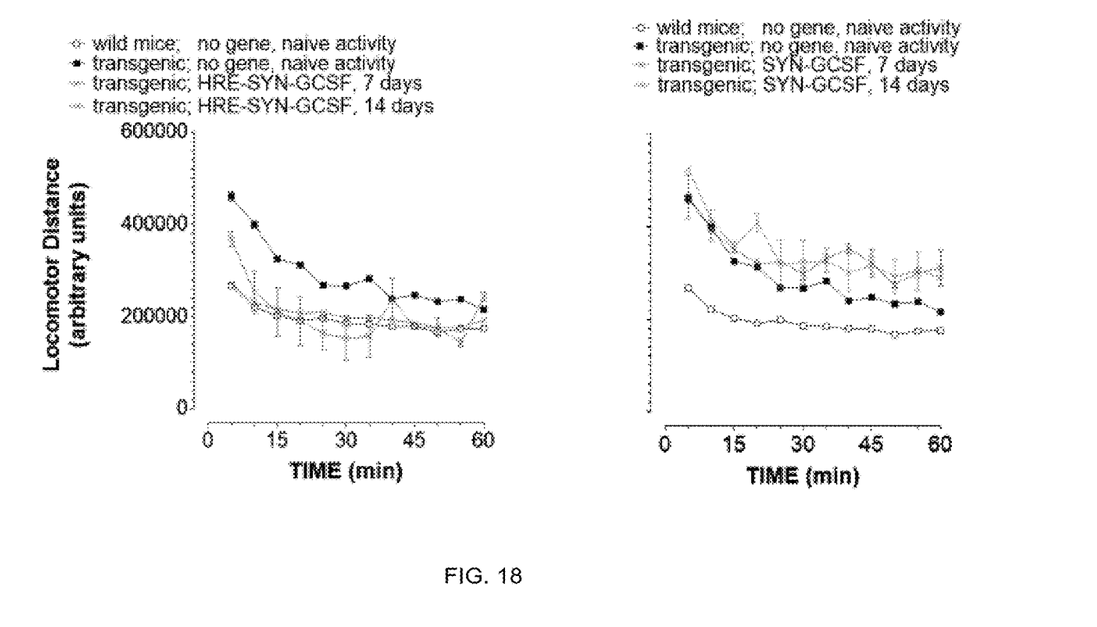
FIG. 18 is a series of graphs showing the effect of GCSF gene therapy on locomotor activity in an animal model for AD.
Figure 19:
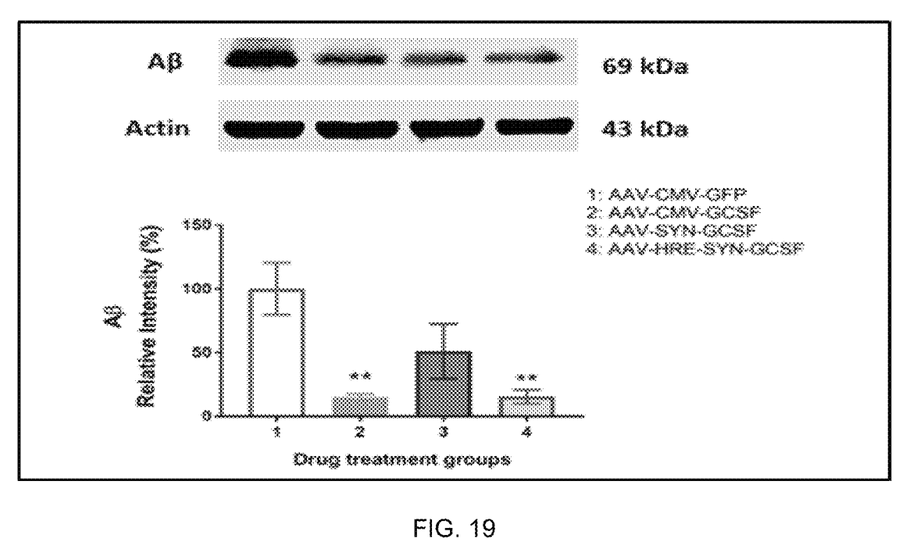
FIG. 19 is a Western blot and a graph showing the effect of GCSF gene therapy on Aβ expression in the BCAO model.
Figure 20:
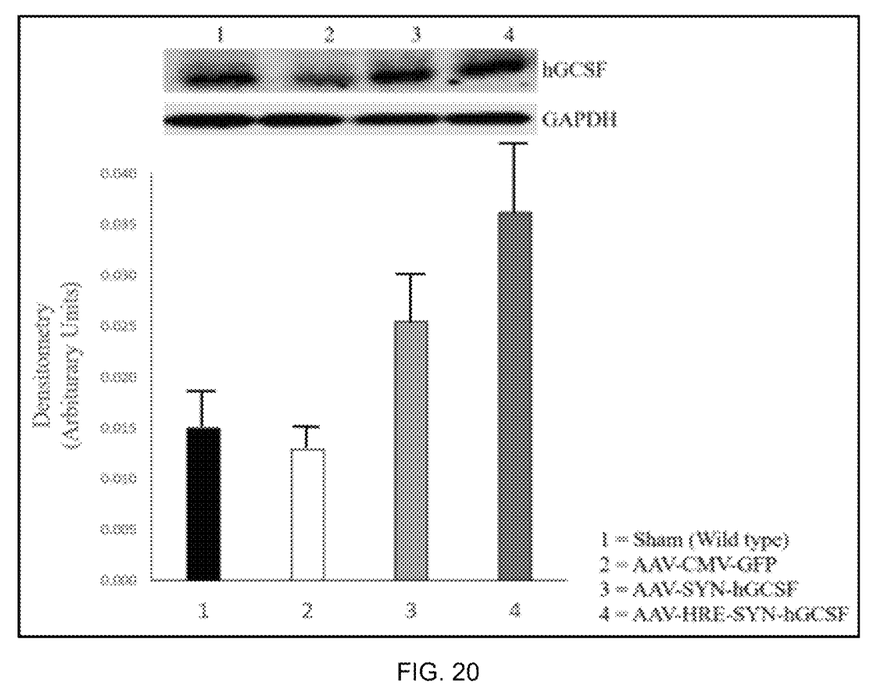
FIG. 20 is a Western blot and a graph demonstrating the expression of hGCSF protein in an AD mouse model after delivery of AAV-hGCSF gene vectors.

Referring to FIG. 18, neuro-protection of GCSF gene therapy was observed in Tg2576 transgenic mouse with mutations on APP KM670/671NL, a genetic-based animal model for AD, using the locomotor activity behavioral test. AAV-HRE-SYN-GCSF gene therapy improved the locomotor activity significantly compared to the group without treatment in the AD model. Referring to FIG. 19, BCAO mice treated with the control vector showed a high level of amyloid-β peptides (Aβ) (Lane 1) while the AAV-GCSF treated groups showed a much lower level of Aβ (Lanes 2, 3, and 4). Referring to FIG. 20, AAV-hGCSF gene vectors administered via the eye drop method increased the expression of hGCSF protein as measured by immunoblotting test. It also increased hGCSF mRNA as measured by qRT-PCR.

Figure 21:
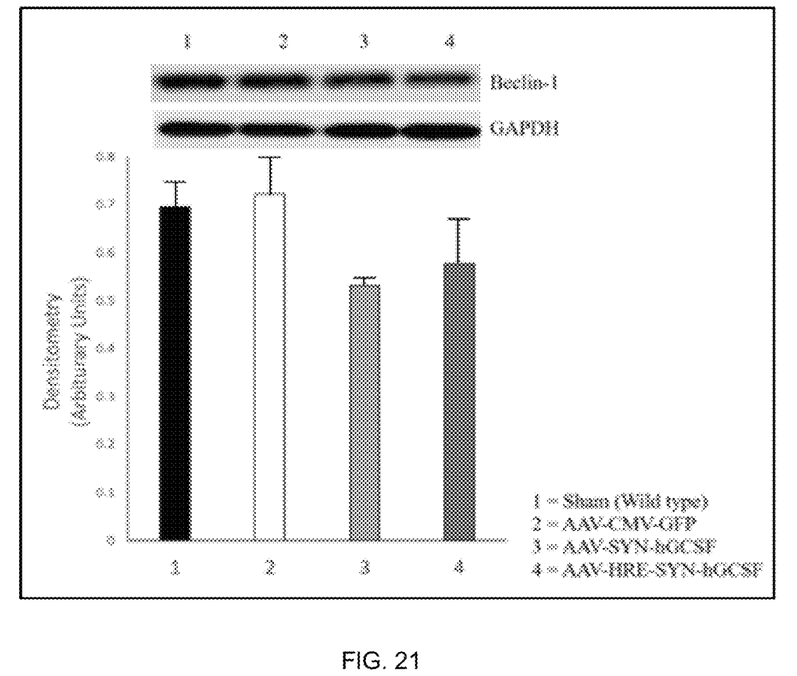
FIG. 21 is a Western blot and a graph showing the effect of AAV-GCSF gene therapy on the expression of Beclin 1 in a transgenic AD animal model.
Figure 22:
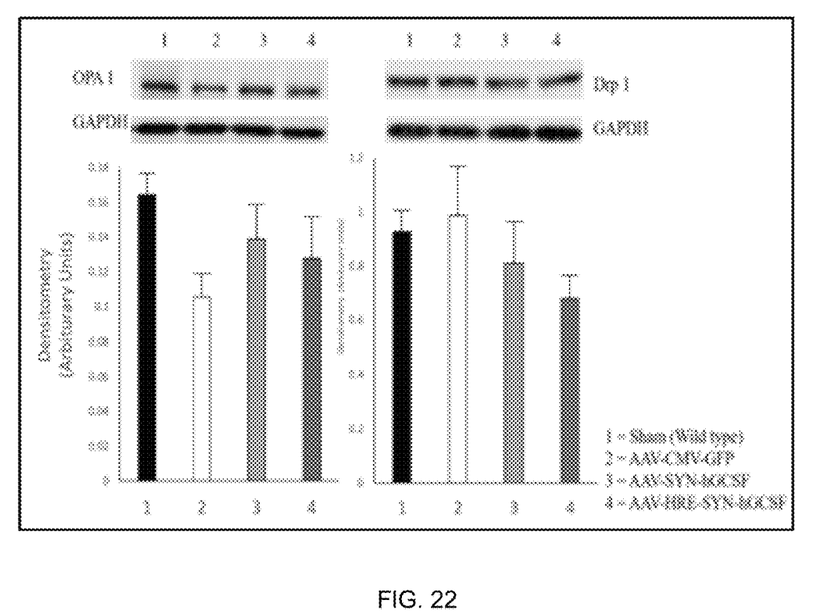
FIG. 22 is Western blots and graphs showing the effect of G-CSF gene therapy on the expression of OPAL and DRP1 in a transgenic AD animal model.
Figure 23:
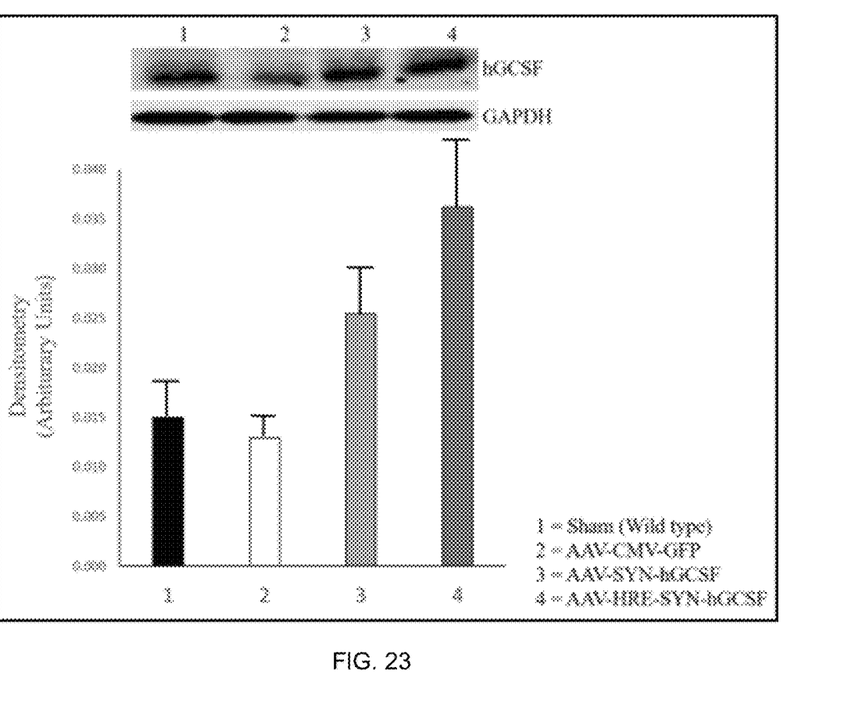
FIG. 23 is a Western blot and a graph showing the effect of G-CSF gene therapy on the expression of GRP78 in a transgenic AD animal model.
Figure 24:
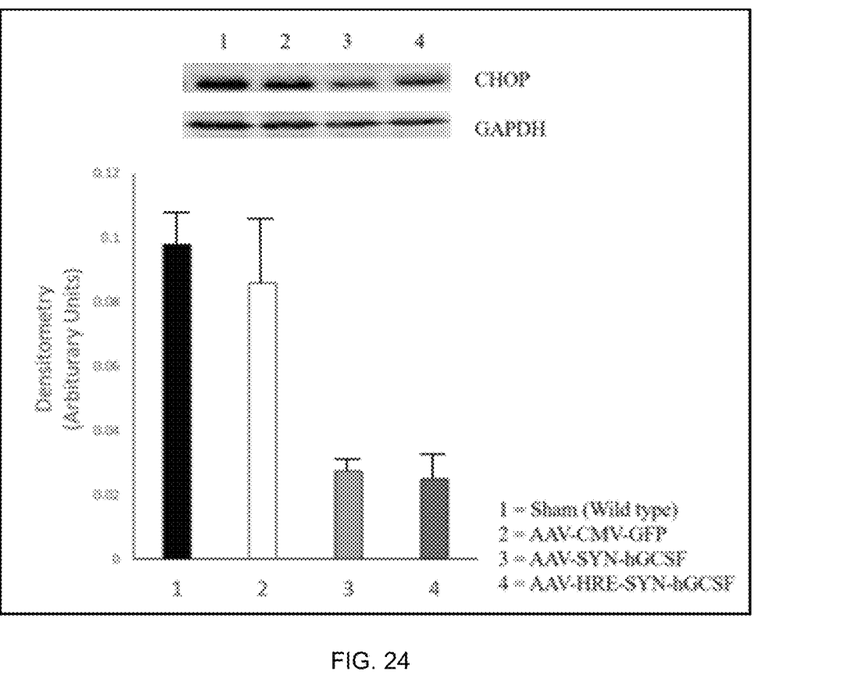
FIG. 24 is a Western blot and a graph showing the effect of G-CSF gene therapy on the expression of CHOP in a transgenic AD animal model.
Figure 25:
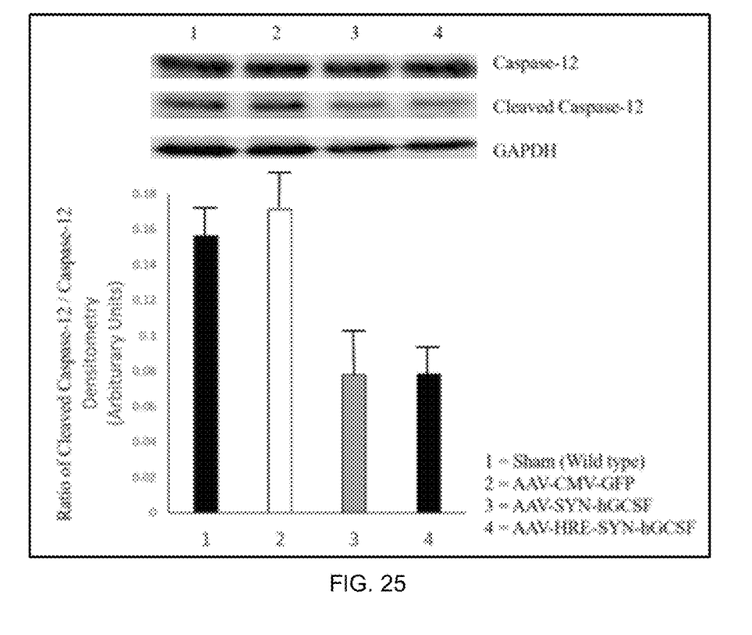
FIG. 25 is a Western blot and a graph showing the effect of G-CSF gene therapy on the expression of Caspase-12 in a transgenic AD animal model.

Referring to FIG. 21, the effect of AAV-SYN-GCSF and AAV-HRE-SYN-GCSF on Beclin 1 in the transgenic AD animal model was evaluated. Beclin 1 showed a reducing trend for the AAV-SYN-hGCSF—treatment (lane 3) and AAVHRE-SYN-hGCSF—treatment (lane 4) in the left section of the brain compared to AAV-CVM-GFP (vehicle; lanes 2). Referring to FIG. 22, the effect of AAV-SYN-hGCSF and AAV-HRE-SYN-hGCSF on OPA1 and DRP1, biomarkers for mitochondrial function in the transgenic AD model was similarly evaluated. A trend for AAV-SYN-hGCSF (lane 3) and AAV-HRE-SYN-hGCSF (Lane 4) to increase OPA1 while decreasing DRP1 compare to AAV-CMV-GFP (vehicle; lane 2) as shown. This suggests that constitutive expression of GCSF by AAV-SYN-hGCSF and AAV-HRE-SYN-hGCSF tends to preserve the mitochondria against fission. The administration of neuronal expression of GCSF, AAV-SYN-hGCSF, and the hypoxic inducible expression of GCSF in neurons, AAV-HRE-SYN-hGCSF, provided greater protection of the mitochondria, since the level of OPA1 and DRP1 were return to the expression level observed in sham (lane 1). Referring to FIG. 23, the effect of expression of AAV-SYN-hGCSF and AAV-HRE-SYN-hGCSF on GRP78, a biomarker for endoplasmic reticulum (ER) stress, was evaluated in the transgenic AD model. The expression level of GRP78 was reduced by the administration of AAV-SYN-hGCSF—treatment (lane 3) and AAV-HRE-SYN-hGCSF—treatment (lane 4) compare to AAV-CVM-GFP (vehicle; lane 2). The reduction of GRP78 was most potent by the hypoxic-inducible expression of GCSF in neurons (AAV-HRE-SYN-hGCSF; lane 4), which suggests that the regulated expression of GCSF in key specific cells (such as neurons) under specific condition (as in the case of hypoxia) trends towards a more effective outcome. Referring to FIG. 24, the effect of expression of AAV-SYN-hGCSF and AAV-HRE-SYN-hGCSF on CHOP, a biomarker (pro-apoptotic) for endoplasmic reticulum (ER) stress, was also evaluated in the transgenic AD model. The expression level of CHOP, the endoplasmic reticulum (ER) stress marker, was reduced by the administration of AAV-SYN-GCSF—treatment (lane 3) and AAV-HRE-SYN-GCSF—treatment (lane 4) compare to AAV-CVM-GFP (vehicle; lane 2). Referring to FIG. 25, the effect of expression of AAV-SYN-hGCSF and AAV-HRE-SYN-hGCSF on Caspase-12, a specific ER membrane-associated caspase, was also evaluated in the transgenic AD model. The expression level of cleaved Caspase12, the endoplasmic reticulum (ER) stress marker, was reduced by the administration of AAV-SYN-GCSF—treatment (lane 3) and AAV-HRE-SYN-GCSF—treatment (lane 4) compare to AAV-CVM-GFP (vehicle; lane 2).

Figure 26:
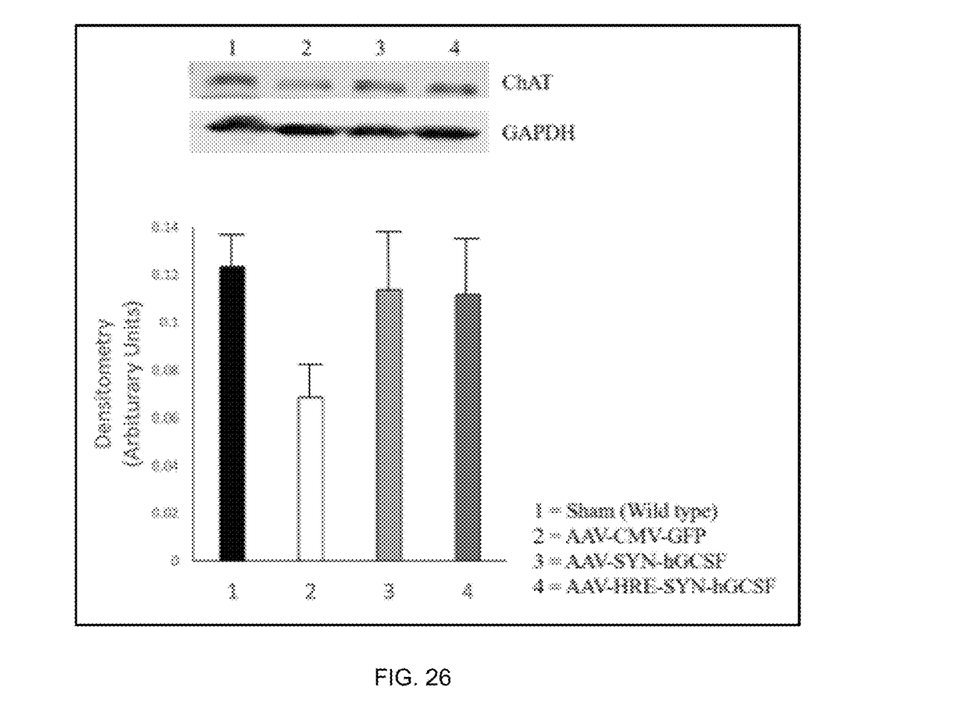
FIG. 26 is a Western blot and a graph showing the effect of G-CSF gene therapy on the expression of choline acetyltransferase (ChAT) in a transgenic AD animal model.

Referring to FIG. 26, the effect of expression of AAV-SYN-hGCSF and AAV-HRE-SYN-hGCSF on choline acetyltransferase (ChAT), a specific marker for cholinergic neurons, was evaluated in the transgenic AD model by immunoblotting with an anti-ChAT antibody. Ach neurons are among the first group of neurons become degenerated in AD. The expression of ChAT was increased by the administration of AAV-SYN-GCSF—treatment (lane 3) and AAV-HRE-SYN-GCSF—treatment (lane 4) compare to AAV-CVM-GFP (vehicle; lane 2).

The therapeutic effects of AAV-hGCSF gene therapy in the transgenic AD model was evaluated. Locomotor activity was conducted at three time points: one day prior delivering gene vectors as naïve (prior sham), day 7 or 14. Genes include AAV-CMV-GFP (control), AAV-SYN-GCSF, or AAV-HRE-SYN-GCSF. Specifically, 5 mice were used to test 7 and 14-day gene therapy. Locomotor activity was significantly increased in Tg2576 mice receiving the control vector, AAV-CMV-GFP, compared to the wild type. The GCSF gene therapy, AAV-HRE-SYN-GCSF, treated group show comparable locomotor activity as the wild type suggesting that AAV-GCSF gene therapy is effective in restoring the locomotor activity of Tg2576 mice to the normal state.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing the volume of a brain infarct that develops in a mammalian subject in response to a cerebral ischemia/reperfusion injury caused by ischemic stroke, the method comprising the step of administering to the eye of the subject a viral vector that comprises a recombinant adeno-associated virus comprising a gene encoding human granulocyte colony stimulating factor (GCSF), a neuron-specific promoter operatively linked with the GCSF gene and an hypoxia-sensitive gene switch/biosensor operatively linked with the GCSF gene, wherein the volume of a brain infarct that develops in the mammalian subject as a result of the cerebral ischemia/reperfusion injury is reduced after administration of the viral vector as compared to the volume of a brain infarct in a subject not treated by administration of the viral vector.

2. The method of claim 1, wherein the viral vector is administered after the ischemic stroke.

3. The method of claim 2, wherein administration of the viral vector reduces brain neuron death in the subject caused by hypoxia.

4. The method of claim 2, wherein administration of the viral vector reduces the amount of neurological deficit in the subject caused by the ischemic stroke.

5. The method of claim 2, wherein administration of the viral vector stimulates neurogenesis in the brain of the subject.

6. A method of treating Alzheimer's disease (AD) in a mammalian subject having elevated levels of brain amyloid-$\beta$ (A$\beta$) and neurological deficit caused by the AD, the method comprising the step of administering to the eye of the subject a viral vector that encodes a granulocyte colony stimulating factor (GCSF) gene.

7. The method of claim 6, wherein administration of the viral vector reduces A$\beta$ levels in brain neurons in the subject.

8. The method of claim 6, wherein administration of the viral vector stimulates neurogenesis in the brain of the subject.

9. The method of claim 6, wherein the viral vector comprises a recombinant adeno-associated virus comprising a gene encoding human GCSF protein.

* * * * *